United States Patent [19]

Salvadori et al.

[11] Patent Number: 5,084,035
[45] Date of Patent: Jan. 28, 1992

[54] DRAINAGE DEVICE

[75] Inventors: Lawrence A. Salvadori; Gerald H. Taylor, both of San Diego, Calif.

[73] Assignee: The Kendall Company, Mansfield, Mass.

[21] Appl. No.: 499,871

[22] Filed: Mar. 27, 1990

[51] Int. Cl.⁵ .................................. A61M 1/00
[52] U.S. Cl. ...................... 604/323; 604/327
[58] Field of Search ........... 604/321, 323, 326, 349, 604/350, 335

[56] References Cited

U.S. PATENT DOCUMENTS

| | | | |
|---|---|---|---|
| 3,415,299 | 12/1968 | Hinman, Jr. et al. | 604/326 |
| 4,010,750 | 3/1977 | Howell | 604/323 |
| 4,417,892 | 11/1983 | Meisch | 604/323 |
| 4,423,741 | 1/1984 | Levy | 604/323 |
| 4,460,362 | 7/1984 | Bates | 604/323 |
| 4,462,510 | 7/1984 | Steer et al. | 604/323 |
| 4,540,156 | 9/1985 | Cross | 604/350 |
| 4,804,375 | 2/1989 | Robertson | 604/323 |

Primary Examiner—Ronald Frinks
Assistant Examiner—R. Clarke
Attorney, Agent, or Firm—Alvin Isaacs

[57] ABSTRACT

A drainage device comprising, a urine receptacle having walls define a chamber, an elastic tubular section having a lumen communicating with the chamber and a distal opening, and a device for simultaneously closing the lumen and covering the distal opening, and for simultaneously opening the lumen and uncovering the distal opening.

24 Claims, 3 Drawing Sheets

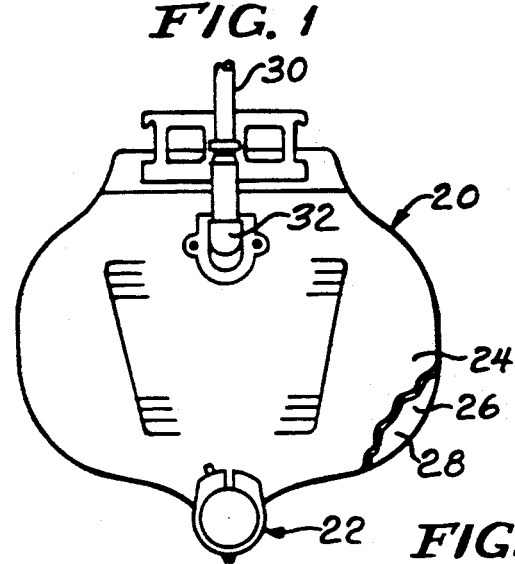
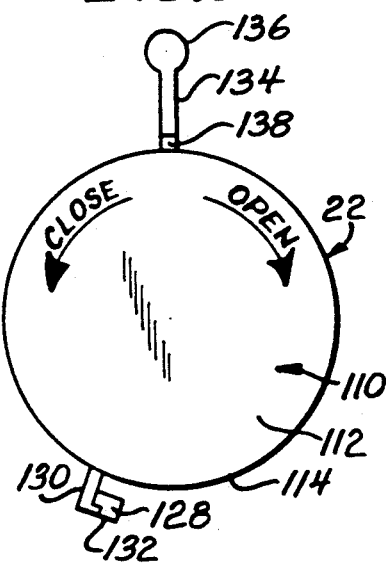
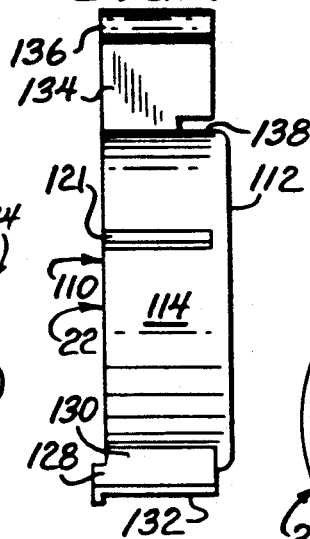
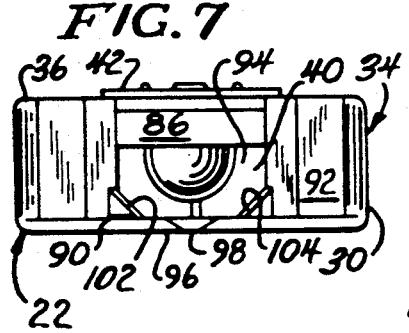
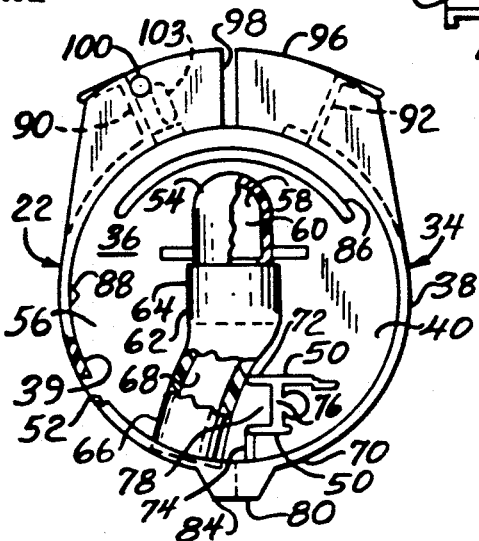
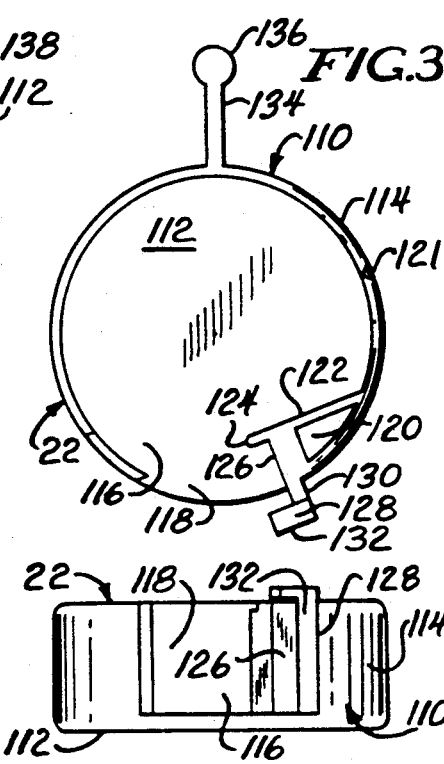
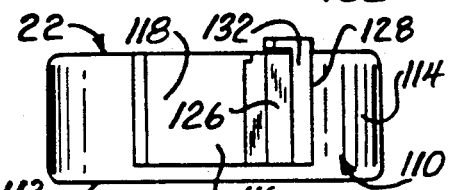
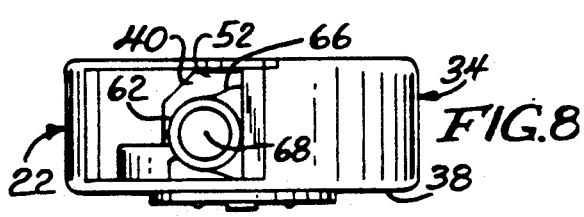

DRAINAGE DEVICE

BACKGROUND OF THE INVENTION

The present invention relates to drainage devices.

Before the present invention, drainage devices, such as urine receptacles or bags, have been known for the collection of urine. Such receptacles may comprise front and back walls joined about their periphery and defining a chamber for the collection of urine. Such drainage receptacles must be periodically emptied of its contents, and, in the past, typically drainage has been accomplished through use of an elastic tubular section communicating a lower end of the chamber, with the tubular section having a releasable clamp closing the tubular section. During use, the clamp is opened in order to permit passage of urine from the drainage receptacle through the tubular section. After drainage has been completed, the clamp is again closed, in order to prevent passage of urine through the tubular section.

It is desirable in the drainage devices to prevent the possibility that urine may inadvertently splash on the user's fingers during emptying of the drainage receptacle.

SUMMARY OF THE INVENTION

A principle feature of the present invention is the provision of an improved drainage device.

The drainage device of the present invention comprises, a urine receptacle having walls defining a chamber, a housing secured to a wall of the receptacle, with the housing having a rear wall, an annular side wall extending from the rear wall, with the rear wall and side wall defining a cavity, with the side wall having a distal opening, and with the housing having a closure member in the cavity adjacent one side of the housing opening. The drainage device has an elastic tubular section in the cavity of the housing communicating with the receptacle chamber and having a lumen and distal opening, with the tubular section extending toward the housing opening over the closure member of the housing. The drainage device has control member pivotally mounted in the housing and having a front wall and an annular side wall extending from the front wall, with the front wall and side wall of the control member defining a cavity, and the side wall of the control member having a distal opening. The control member has a closure member. A side wall of the control member is received in the housing cavity with the front wall of the control member closing the housing cavity, with the closure member of the control member being located on a side of the tubular section opposite the closure member of the housing, with the control member being slidably mounted in the housing and being moveable between a first position with the closure member of the control member spaced a sufficient distance from the closure member of the housing to open the lumen with the opening of the closure member being in register with the housing opening, and a second position with the closure member of the control member and closure member of the housing engaged against the tubular section to close the lumen.

A feature of the present invention is that the control member is a releasable locked in the second position in order to assure closure of the device.

Thus, a feature of the present invention is that the control member is positively locked in the second closure position.

A further feature of the invention is that the control member and housing render an audible sound when opening and closing the device in order that the user knows the condition of the drainage device.

Still another feature of the invention is that the control member is operated by a lever which projects in a direction away from the distal end of the tubular section.

A feature of the present invention is that the lever and attached control member may be operated by the user's fingers at a location spaced a substantial distance away from the draining urine in order to prevent the possibility of urine splashing against the user's fingers during drainage and operation of the device.

A further feature of the invention is that the housing and control member close a distal end of the tubular section in the second position of the control member in order to further ensure against the possibility of urine leakage from the drainage device.

Yet another feature of the invention is that the control member closes the lumen of the tubular section simultaneously with covering the distal end of the tubular section to further ensure that urine is removed from the tubular section, and that drainage from the device is prevented.

Another feature of the invention is that the closure members of the control member and housing include planar walls intermediate the respective flange and recess of the closure members and the distal end of the tubular section in order to squeeze urine from the tubular section while being closed.

Still another feature of the invention is that the control member may be operated through the use of one hand in opening and closing the closure members.

Another feature of the invention is that the drainage device is simple to operate.

A further feature of the invention is that the drainage device is of compact construction.

Yet another feature of the invention is that the housing and associated control member and tubular section do not extend substantially below a lower level of the urine receptacle.

A further feature of the invention is that the tubular section faces downwardly from the urine receptacle during use of the drainage device.

Another feature of the invention is that the control member is releasably locked to the housing in a simplified manner.

A further feature of the invention is that the drainage device has a member to provide friction between the housing and rotating control member in order to provide control over the flow of urine at a selected rate through the tubular section.

Another feature of the invention is that when the closure member of the control member closes against the closure member of the housing any drops of urine are squeezed out of the distal end of the tubular section.

Thus, a feature of the invention is that subsequent to closure of the control member to the second position, no urine remains the closure portion of the drainage device.

Thus, in this manner, the drainage device also minimizes the possibility of splashing of urine against the user's hands.

Further features will become more fully apparent in the following description of the embodiments of this invention and from the appended claims.

DESCRIPTION OF THE DRAWINGS

In the drawings:

FIG. 1 is a plan view, partly broken away, of a drainage device of the present invention;

FIG. 2 is a front plan view of a closure member for the drainage device of FIG. 1;

FIG. 3 is a rear plan view of the closure member of FIG. 2;

FIG. 4 is an elevational view taken substantially as indicated along the line 4—4 of FIG. 3;

FIG. 5 is a lower plan view taken substantially as indicated along the line 5—5 of FIG. 3;

FIG. 6 is a front plan view of a housing for the drainage device of FIG. 1;

FIG. 7 is a top plan view taken substantially as indicated along 7—7 of FIG. 6;

FIG. 8 is a bottom plan view taken substantially as indicated along 8—8 or FIG. 6;

DESCRIPTION OF THE PREFERRED EMBODIMENTS

Figure 9:
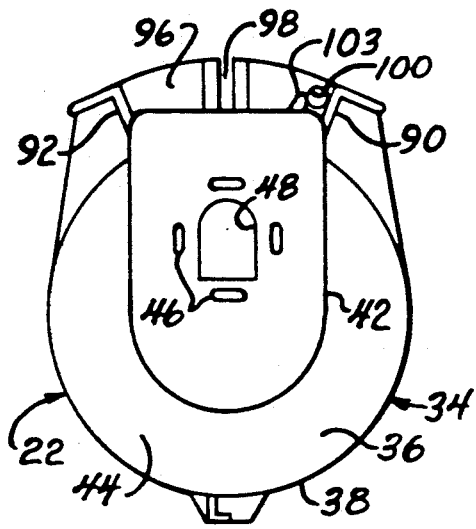
FIG. 9 is a rear plan view of the housing of FIG. 6.
Figure 10:
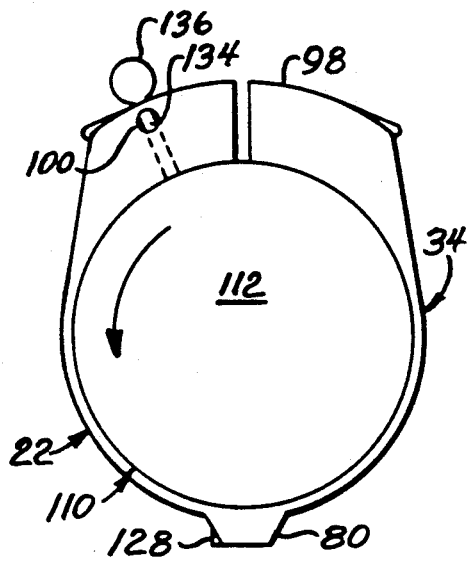
FIG. 10 is a front plan view of the drainage device of FIG. 1, with a closure member of the drainage device being located in a closed position.
Figure 12:
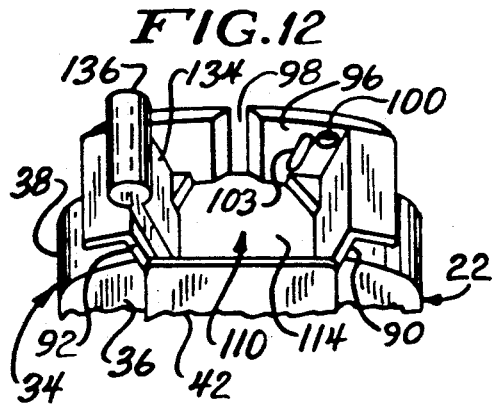
FIG. 12 is a fragmentary perspective view of the drainage device of FIG. 1.
Figure 11:
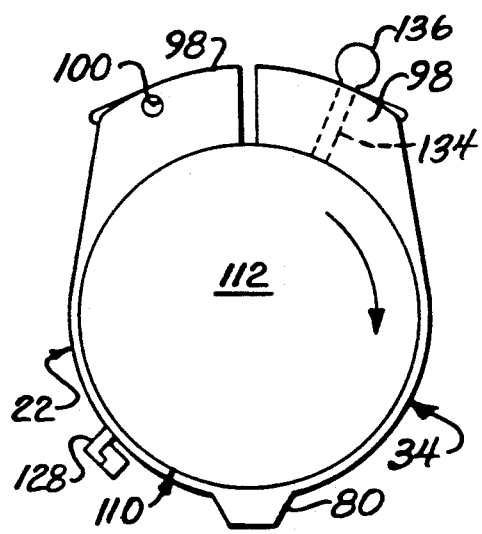
FIG. 11 is a front plan view of the drainage device of FIG. 1, with the closure member located in an open position.
Figure 14:
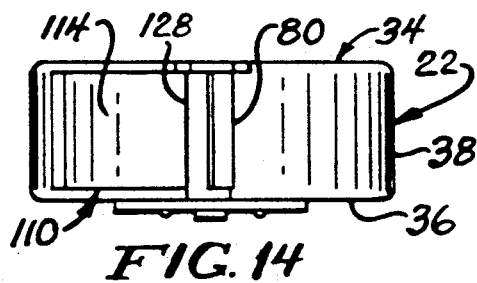
FIG. 14 is a bottom plan view of the drainage device of FIG. 1, with the closure member in a closed position.
Figure 13:
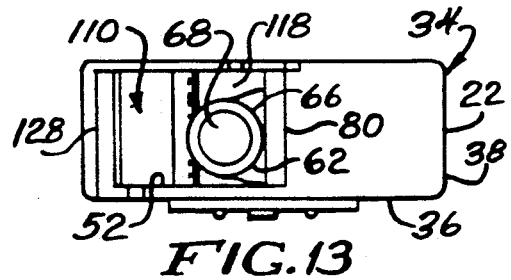
FIG. 13 is a bottom plan view of the drainage device of FIG. 1, with the closure member in an open configuration.
Figure 15:
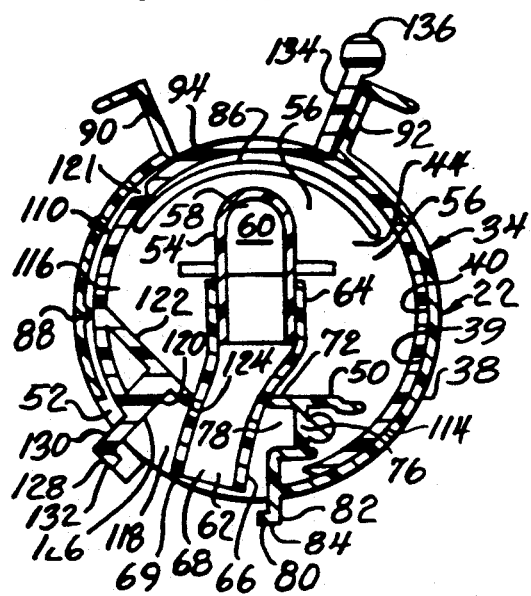
FIG. 15 is a sectional view of the drainage device of FIG. 1, with the closure member in an open configuration.
Figure 16:
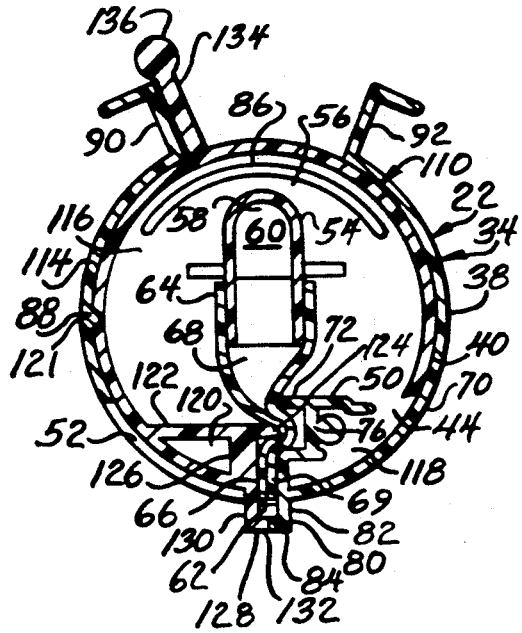
FIG. 16 is a sectional view of the drainage device of FIG. 1, with the closure member in a closed position.

Referring now to FIG. 1, there is shown a drainage receptacle generally designated 20, such as a urine bag, and a drainage device generally designated 22 secured to a lower portion of the drainage receptacle 20. The drainage receptacle 20 has a front wall 24 of flexible material, and a rear wall 26 of flexible material, with the front and rear walls 24 and 26 being joined at their periphery to define a chamber 28 intermediate the front and rear walls 24 and 26. The drainage receptacle 20 has a drainage tube 30 communicating with a connector 32 attached to the front wall 24 and communicating with the chamber 32, such that urine drains through the drainage tube 30 and connector 32 into the chamber 28 for collection therein.

With reference to FIG. 6-16, the drainage device 22 has an outer housing generally designated 34 having a rear wall 36, and an annular side wall 38 extending from the rear wall 36, with the rear wall 36 and side wall 38 defining a cavity 40. As best shown in FIG. 9, the drainage device 22 has a flexible securement member 42 secured to a rear surface 44 of the rear wall 36 by suitable means, such as heat sealing. The securement member 42 has a plurality of bosses 46 extending around an inlet port 48 in the securement member 42. The securement member 42 is secured to an outer surface of the front wall 24 of the drainage receptacle 20, with the inlet port 48 of the securement member 42 in register with an opening in a lower portion of the front wall 24.

With reference to FIG. 6-16, the housing side wall 38 has a closure member 50 located adjacent a distal or outer end of the housing 34, and extending from the side wall 38 into the cavity 40. The housing 34 also has a distal opening 52 located adjacent the closure member 50 of the housing 34. As shown, the housing 34 has a tubular member 54 secured to a front surface 56 of the rear wall 36, with a passageway 58 of the tubular member 54 being in communication with a port 60 extending through the rear wall 36 in registration and communicating with the inlet port 48 of the securement member 42. The tubular member 54 extends vertically from the rear wall 36 into the cavity 40 and is formed at generally 90 degrees in a bend toward the distal opening 52. The housing 54 has an elastic tubular section 62 having a proximal end 64 secured to a distal end 66 of the tubular member 54 with a lumen 68 extending through the tubular section 62 and communicating with the passageway 58 of the tubular member 54. As shown, the tubular section 62 extends along a side of the closure member 50 with a distal end 69 of the tubular section 62 being located adjacent an outer surface 70 of the side wall 38 in the distal opening 52.

The closure member 50 has an outer flange 72 connected to a generally planar inner portion 764 by a rib 76, with the flange 72, inner portion 74, and rib 765 defining a recessed 78 facing toward the tubular section 62, and with the inner portion 74 of the closure member 50 extending from the side wall 38 at one side of the distal opening 52.

The housing 34 has an end cap 80 adjacent a side of the distal opening 52 in the vicinity of the closure member 50. The end cap 80 of the housing 34 has an outwardly directed flange 82 at the side of the housing opening 52, and an outer end portion 84 directed toward the housing opening 52 and located distal the distal end 69 of the tubular section 62.

The housing 34 has an arcuate flange 86 extending from the rear wall 36 into the cavity 40, and spaced slightly from the side wall 38 of the housing 34. As shown, the housing 34 has an inwardly directed boss or rib 88 extending from an inner surface 38 of the side wall 38 into the cavity 40.

The housing 34 has a pair of spaced outwardly directed walls 90 and 92 defining an aperture 94 extending through the side wall 38 on a side of the housing 34 opposed to the distal opening 52. The housing 34 has a front cover member 96 extending substantially between the walls 90 and 92 and being generally aligned with the front of the housing 34. The cover member 98 has a generally central slot 98 extending through the cover member 96. Also, the cover member 96 has an aperture 100 extending through the cover member 96 adjacent the wall 90 for a purpose which will be described below. The housing 34 also has a pair of opposed beveled flanges 102 and 104 extending between the walls 90 and 92, respectively, and the cover member 96 for a purpose which will be described below.

With reference to FIGS. 2-5 and 9-16, the drainage device 22 has a control member generally designated 110 having a front wall 112, and an annular side wall 114 extending from the front wall 112, with the front wall 112 and side wall 114 defining a cavity 116, and with the side wall 114 of the control member 110 having a distal opening 118.

The control member 110 has a closure member 120 located on a side of the distal opening 118 in the cavity 116. The closure member 120 has an outer flange 122 with an outwardly directly boss 124 projecting toward a side of the tubular section on an opposed side of the closure member 50 of the housing 34, and at a location directed toward the recess 78 of the closure member 50. Also, the closure member 120 of the control member 110 has a generally planar inner portion 126 extending from the flange 122 to the side wall 114 at a side of the distal opening 118.

As shown, the control member 110 has an outer end cap 128 located adjacent the side of the opening 118 of the control member 110 in the proximity of the closure member 120 of the control member 110. The end cap 128 has an outwardly directed flange 130 adjacent the side of the distal opening 118, and an outer end portion 132 directed toward the distal opening 118, with the end portion 132 of the end cap 128 being located distal the distal end 69 of the tubular section 62.

The control member 110 has an outwardly directed lever 134 extending from the sidewall 114 of the control member 110 on a side opposite the distal opening 118, with the lever 134 having an outer knob 136. The lever 134 has an inner notch 138 adjacent the front wall 112 for a purpose which will be described below.

In use, the control member 110 is assembled in the housing 34 in the following manner. First, the end cap 128 of the control member 110 is inserted into the distal opening 52 of the housing 34, and the lever 134 of the control member 110 is inserted through the slot 98 of the cover member 96 until the side wall 114 of the control member 110 is located in the cavity 40 of the housing 34. In this configuration, the side wall 114 of the control member 110 is located inside the side wall 38 of the housing 34, and the control member 110 is slidably or pivotally mounted in the housing 34 with the side wall 114 of the control member 110 sliding inside the side wall 38 of the housing 34.

The control member 110 is moveable between a first open position with the closure member 120 of the control member 110 spaced a sufficient distance from the closure member 50 of the housing 34 to open the lumen 68 of the tubular section 62, with the distal opening 118 of the control member 110 being in registration with the distal opening 52 of the housing 34, and a second closure position with the closure member 120 of the control member 110 and closure member 50 of the housing 34 engaged against opposed sides of the tubular section 62 to close the lumen 68 of the tubular section 62.

In the first position of the control member 110, the closure member 120 of the control member 110 and spaced closure member 50 of the housing 34 permit passage of urine through the lumen 68 of the tubular section 62 from the chamber 28 of the drainage receptacle 20. in order to drain the urine from the receptacle 20. In this configuration, the end cap 128 of the closure member 110 is spaced from the end cap 80 of the housing 34, such that passage of urine is permitted through the registered openings 118 and 52 and the spaced end caps 128 and 80.

In the second position of the control member 110, the boss 88 of the housing 34 is releasable received in the groove 121 of the control member 110 in order to releasably lock the control member 110 in its second position relative to the housing 34. The boss 88 and groove 121 make an audible sound when then engage with each other in the second position of the control member 110 in order to signify the user of this condition. Also, in this configuration, the flange 102 is received in the notch 138 of the lever 134, and the lever 134 is received intermediate the rib 103 and wall 90 in order to also facilitate releasable locking of the control member 110 in the second position. Further, the lever 134 is aligned with the aperture 100 to signify to the user that the control member 110 is in the second position through vision of the lever 134 through the aperture 100 of the cover member 98 of the housing 34.

In the first position of the control member 110, the lever 134 is located adjacent the wall 92, and the end cap 128 is located adjacent a side of the distal opening 52. Further, the flange 104 is received in the notch 138 of the lever 134. The boss 88 frictionally engages against the outer surface of the side wall 114 of the control member 110 in order to impede movement of the control member 110 relative to the housing and provide control of the control member as it is moved between the first open position and the second closed position, and thus control the flow of urine through the tubular section 62 with the tubular section 62 being partially closed.

As the control member 110 moves to its second position, the end portion 132 of the end cap 128 of the control member 110 presses the tubular section 62 against the end portion 84 of the end cap 80 of the housing 84 in order to squeeze out any drops of urine from the lumen 68 of the tubular section 62 during closure of the control member 110 in order to minimize the possibility of splashing of urine against the user's hands by removing urine at a location distal the recess 78 of the closure member 50 and the flange 130 of the closure member 120 of the control member 110. Further, the flange 130 of the closure member 120 of the control member 110 is received in the recess 78 of the closure member 50 of the housing 34 in order to close the lumen 68 of the tubular section 62 and prevent passage of urine through the tubular section 62. In addition, the end cap 128 of the control member 110 closure against the end cap 80 of the housing 34 in order to close the distal end of the tubular section 62, thus preventing the possibility of splashing of urine from the drainage device 22. Further, the closure member 120 of the control member 110 and closure member 50 of the housing 34 and the respective end caps 128 and 80 simultaneously close and open the tubular section 62 at the same time that the end caps 128 and 80, respectively, close and open the distal end of the tubular section 62. Further, since the lever 134 is located remote the distal end of the tubular section 62, the drainage device 62 further assures that urine will not splash from the tubular section 62 onto the user's fingers while manipulating the lever 134. In addition, the drainage device 22 is easy to operate by one hand of the user by manipulating the lever 134 relative to the walls 90 and 92 of the housing 34, and the control member 110 is releasably locked in the second closure position in a simplified manner.

Figure 17:
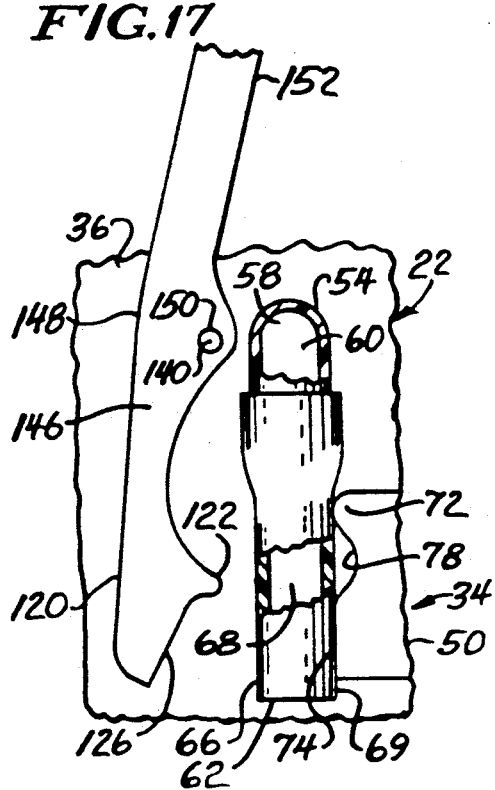
FIG. 17 is a front plan view of another embodiment of the drainage device of the present invention with a lever member of the device in an open configuration.
Figure 18:
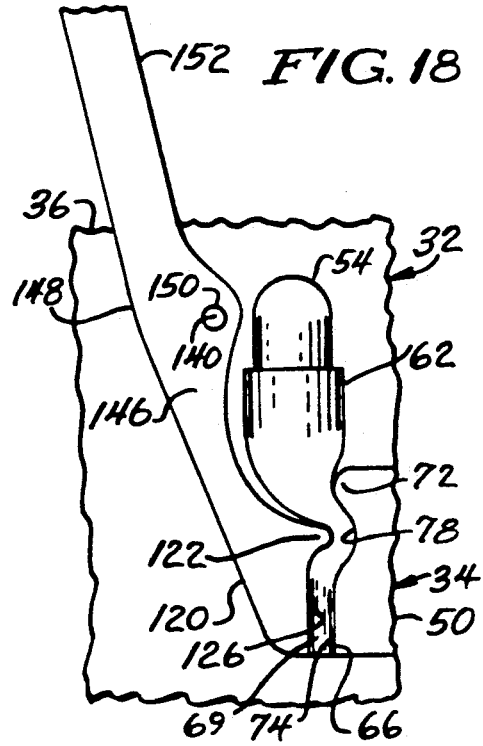
FIG. 18 is a front plan view of the drainage device of FIG. 17, with the lever member in a closed configuration.

Another embodiment of the present invention is illustrated in FIGS. 17 and 18, in which like reference manuals designate like parts. In this embodiment, the drainage device 22 has a generally planar housing 34 having an upper pivot pin 140 extending from the rear wall 36 of the housing 34. The housing 34 has a tubular member 54 extending from a port 60 in the rear wall 36 and communicating with the chamber of the receptacle, and the tubular member 54 is connected to an elastic tubular section 62 having a lumen 68, as previously discussed. As shown, the tubular section 62 is located on a side of a closure member 50 of the housing 34, with the closure member 50 having an outer flange 72, a generally planar inner portion 74, and a recess 78 intermediate the flange 72 and inner portion 74 facing toward the tubular section 62.

The drainage device 22 has a lever member 146 having a central portion 148 having an aperture 150 pivotally received on the pin 140 of the housing 34. The lever member 146 has an outer handle 152 for manipulating the lever member 146 about the pin 140. The lever member 146 also has a closure member 120 having an outwardly directed flange 122 facing toward the tubular section 62, and a generally planar portion 126 facing toward the tubular section 62.

Thus, in use, the lever member 146 may be moved between a first position with the closure member 120 of the lever member 146 spaced from the tubular section 62 in order to permit passage of urine from the drainage receptacle through the tubular member 54 and tubular section 62, and a second position with the closure member 120 of the lever member 146 being engaged against the tubular section 62, with the flange 122 of the lever member 146 received in the recess 78 of the closure member 50 of the housing 34 in order to close the lumen 68 of the tubular section 62 while the planar portion 126 of the closure member 120 closes the distal portion of the tubular section 62 against the planar portion 74 of the closure member 50, as previously discussed. In other respects, the drainage device 22 of FIGS. 17 and 18 operate substantially in the same manner as the drainage device 22 discussed in connection with FIGS. 1-16.

The foregoing detailed description is given for clearness of understanding only and no unnecessary limitations should be understood therefrom, as modifications will be obvious to those skilled in the art.

What is claimed is:

1. A drainage device, comprising:
    a urine receptacle having walls defining a chamber; a housing having a rear wall, an annular side wall extending from the rear wall, with the rear wall and side wall defining a cavity, said side wall having a distal opening, and said housing having a closure member in the cavity adjacent one side of the distal opening;
    an elastic tubular section in the cavity of the housing communicating with the receptacle chamber and having a lumen and a distal opening, said tubular section extending toward the housing opening over the closure member of the housing;
    a control member pivotally mounted in the housing and having a front wall and an annular side wall extending from the front wall, with the front wall and side wall of the control member defining a cavity, with the side wall of the control member having a distal opening, and with said control member having a closure member, said side wall of the control member being received in the housing cavity with the front wall of the control member closing the housing cavity, and with the closure member of the control member being located on a side of the tubular section opposite the closure member of the housing, said control member being slidably mounted in the housing and being moveable between a first position with the closure member of the of the control member spaced a sufficient distance from the closure member of the housing to open the lumen of the tubular section and with the opening of the closure member being in register with the opening of the housing, and a second position with the closure member of the control member and closure member of the housing engaged against the tubular section to close the lumen, said device further including an arcuate flange extending from the rear wall of the housing into the housing cavity, with said flange engaging against an inner surface of the side wall of the control member.

2. The device of claim 1 wherein the side wall of the control member closes the housing opening in the second position of the control member.

3. The device of claim 1 wherein the side wall of the control member is slidably mounted in the side wall of the housing.

4. The device of claim 1 wherein the rear wall of the housing has an inlet port communicating with the receptacle chamber, and in which the lumen of the tubular section communicates with the inlet port.

5. The device of claim 4 including a tubular member extending from the rear wall of the housing and having a passageway communicating with the port, said tubular member being connected to a proximal end of the tubular section with the passageway communicating with the lumen.

6. The device of claim 5 wherein the tubular member has a bend of approximately 90 degrees, with a distal end of the tubular member being generally directed toward the housing opening.

7. The device of claim 1 wherein a distal end of the tubular section is located adjacent the housing opening.

8. The device of claim 1 wherein one of the closure members has a recess, and the other of the closure members has a flange received in the recess in the second position of the control member to close the lumen of the tubular section.

9. The device of claim 8 wherein the one closure member has a wall extending distally from the recess, and the other closure member has a wall extending from the flange such that the walls of the closure members engage against a length of the tubular section distal the recess and flange to close a distal length of the tubular section.

10. The device of claim 9 wherein the walls of the closure members are generally planar.

11. The device of claim 9 wherein the walls of the closure member extend past a distal end of the tubular section.

12. The device of claim 1 wherein the housing has an end cap adjacent a side of the housing opening, and in which the control member has an end cap adjacent a side of the opening of the control member, said end cap closing over the port of the tubular section in the second position of the control member.

13. The device of claim 12 wherein the cap of the housing has an outwardly directed flange at the side of the housing opening, and an outer end portion directed toward the housing opening, and in which the cap of the control member has an outwardly directed flange at the side of the control member, and an outer end portion directed toward the opening of the control member.

14. The device of claim 1 wherein closure member of the housing has a wall defining an inner recess adjacent the tubular section, an outer cap distal the tubular section, and a closure portion intermediate the recess and end cap, and in which the control member has a wall defining a flange adjacent with the housing recess, an outer end cap distal the tubular section which closes against the end cap of the housing, and a closure portion intermediate the flange end cap to engage the tubular section against the closure portion of the housing.

15. The device of claim 1 wherein the side wall of one of said housing and control member has a boss, and the side wall of the other of said housing and control member has a recess to receive the boss in the second position of the control member and releasable lock the control member in the second position.

16. The device of claim 1 wherein the side wall of the housing has an inner flange, and in which the side wall of the control member has an outer groove to receive the flange at the second position of the control member to releasably lock the control member in the second position.

17. The device of claim 1 wherein the housing has a pair of spaced outwardly directed walls defining an aperture opposed from the housing opening, and in which the control member has an outwardly directed lever received in the housing aperture and being moveable between the spaced walls in the first and second positions of the control member.

18. The device of claim 17 wherein the lever extends outwardly from the spaced walls.

19. The device of claim 17 wherein the housing has a front cover member extending substantially between the spaced walls and being generally aligned with the front wall of the control member.

20. The device of claim 19 wherein the cover member has an aperture aligned with the lever in the second position of the control member.

21. The device of claim 17 wherein the cover member has a generally central slot to receive the lever during assembly of the control member in the housing.

22. The device of claim 17 wherein the cover member has an inner boss adjacent one of the spaced walls to releasable receive the lever intermediate the boss and one wall.

23. The device of claim 17 wherein the housing has a pair of flanges adjacent opposed sides of the aperture, and in which the lever has a slot to receive the flanges in the first and second positions of the control member.

24. The device of claim 1 including a flexible securement member connected intermediate the rear wall of the housing and a front wall of the receptacle.

* * * * *